United States Patent [19]

Curry

[11] Patent Number: 4,658,931

[45] Date of Patent: Apr. 21, 1987

[54] EVACUATED PLENUM HEARING PROTECTION

[76] Inventor: David G. Curry, P.O. Box 683, Bayou La Batre, Ala. 36509

[21] Appl. No.: 743,345

[22] Filed: Jun. 11, 1985

[51] Int. Cl.⁴ .................... H04R 25/00; A61B 7/02
[52] U.S. Cl. ................... 181/129; 181/135; 381/187
[58] Field of Search ............. 181/129, 135, 130, 126; 179/156 R, 182 R, 182 A, 180

[56] References Cited

U.S. PATENT DOCUMENTS

| | | | |
|---|---|---|---|
| 2,782,423 | 2/1957 | Simon et al. | 2/209 |
| 2,990,553 | 7/1961 | Ulrich et al. | 2/209 |
| 3,117,575 | 1/1964 | Carrell et al. | 181/129 X |
| 3,602,239 | 8/1971 | Bauer | 181/129 |
| 3,621,488 | 12/1971 | Gales | 181/129 X |
| 3,644,939 | 2/1972 | Beguin | 2/209 |
| 3,661,225 | 5/1972 | Anderson | 181/129 X |
| 3,845,505 | 11/1974 | Davidson et al. | 2/209 |
| 4,114,197 | 9/1978 | Morton | 2/423 |

*Primary Examiner*—Benjamin R. Fuller
*Attorney, Agent, or Firm*—Gerald B. Hollins; Donald J. Singer

[57] ABSTRACT

Protection apparatus for excluding undesirable noise from the eardrum and inner ear of a user. The disclosed apparatus includes an evacuated, transmission medium-free, cavity for attenuating the noise energy. Plural arrangements of the evacuated cavity between the eardrum and noise environ are included. Uses of the disclosed protection apparatus in several military and industrial applications are described, including applications wherein communication with the protection user is needed.

5 Claims, 3 Drawing Figures

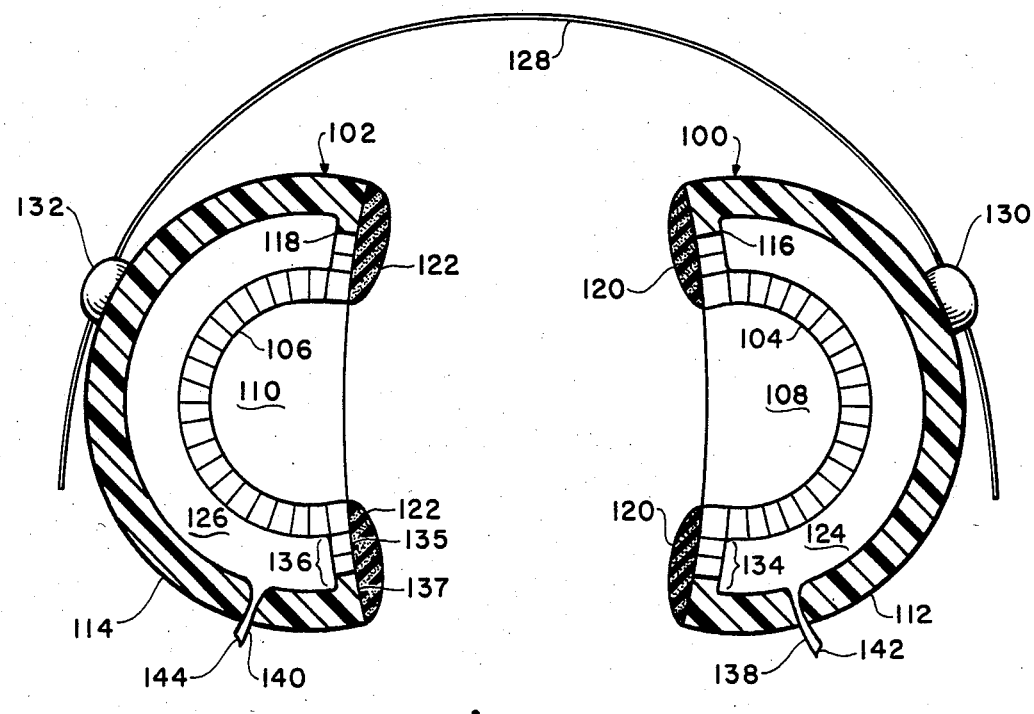
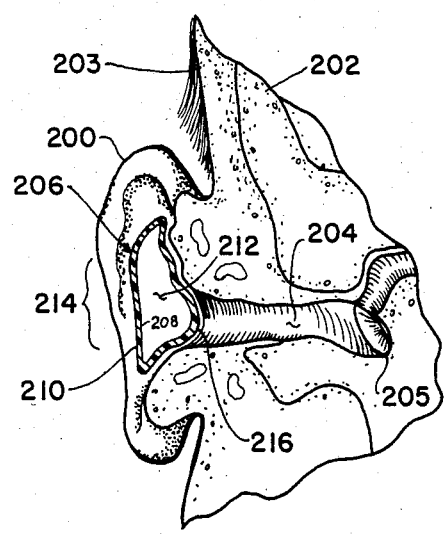 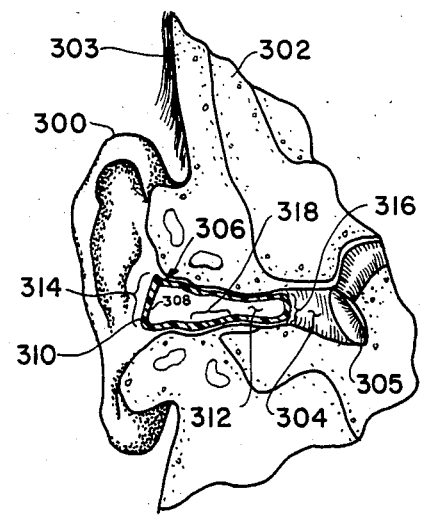

EVACUATED PLENUM HEARING PROTECTION

RIGHTS OF THE GOVERNMENT

The invention described herein may be manufactured and used by or for the Government of the United States for all governmental purposes without the payment of any royalty.

BACKGROUND OF THE INVENTION

This invention relates to the field of hearing protection capable of excluding noise and other sounds from the ears of a protected person.

Persons obligated to work in loud noise environments are known to incur premature hearing loss and other abnormal medical conditions. In the past, workers who participated in the riveting of heavy structures, steam locomotive engineers, saw mill operators and certain types of mineral miners provided notable examples of hearing loss originating in prolonged exposure to impact and other high intensity noises. In modern times, persons working on aircraft flight lines, in electrical power generation plants, crewmembers in Navy gun turrets and armored tank crewmembers are typical of those found to be susceptible to noise-induced hearing loss. The recent advent of Occupational Safety and Health Administrations (OSHA) in the federal and state governments has increased the awareness and knowledge needed in preventing prolonged exposure hearing injuries. The OSHA rules relating permissible exposure time inversely with noise intensity have been particularly effective in diminishing the incidence of work-related hearing injuries.

Such new awareness together with the inherent preference of human workers to be minimally encumbered with bulky and heavy hearing protection apparatus has created an ongoing need for improved hearing protection arrangements, preferably arrangements based on new technology protective concepts. The need for such new concepts in hearing protection is particularly acute in many military situations where such complexities as confined space, long mission durations, frequent personnel changes, and a need to communicate with heating protected persons add complexity to the hearing protection problem.

The absence of a fully satisfactory hearing protection arrangement in the prior art is exemplified by the number of different hearing protection devices found in prior patents. Among these previous hearing protection arrangements is the ear protector of E. Simon et al, shown in U.S. Pat. No. 2,782,423. The Simon apparatus is similar to the earphone devices used in radio and telegraph communications. The Simon apparatus includes ear enclosing pads which are fabricated from a plastic foam, preferably an isocyanate plastic foam capable of absorbing sound energy and particularly the sound emitted by an aircraft jet engine.

The patent of R. E. Ulrich et al, U.S. Pat. No. 2,990,553, discloses an ear protection arrangement employing a paste-like consistency liquid mixture as a sound attenuating medium.

In the patent of F. P. Beguin, U.S. Pat. No. 3,644,939, is disclosed a hearing protector ear cup provided with a venting arrangement that is compatible with achieving low frequency sound attenuation. The Beguin patent includes a cup-like cavity and a resilient padding member for engagement with the ear adjacent skin tissue of a user subject.

The patent of E. L. Davidson et al, U.S. Pat. No. 3,845,505, describes a suspension arrangement for adjusting the position of noise attenuating ear cups with respect to an attached safety helmet. The Davidson et al sound attenuation material is made from foam rubber or plastic and is incorporated within a cup-like receptacle.

In the patent of W. G. Morton, U.S. Pat. No. 4,114,197, a safety helmet having an ear protecting sub-portion is disclosed. The Morton protector includes inner and outer cavity members in a double walled structure intermediate the user's ear and an external source of sound. The inner cavity in the Morton apparatus is fitted with a resilient member which contacts the skin of the user's cranial surface.

Although each of these previously patented hearing protection arrangements employs a cup-like structure and a suspension arrangement similar to that used in the present invention, none of these prior devices achieves the advantages of sound attenuation through the present invention's non-conductive medium.

SUMMARY OF THE INVENTION

An object of the present invention is to provide a hearing protection arrangement which employs the non-sound conductive properties of an evacuated chamber for attenuating sound energy reaching the user's ear.

Another object of the invention is to provide an evacuated chamber sound attenuation apparatus which may be configured in a variety of different physical arrangements.

Another object of the invention is to provide a hearing protection arrangement which can be fabricated in a lightweight, low-mass form.

Another object of the invention is to provide a hearing protection apparatus capable of long and trouble-free service.

Another object of the invention is to provide a hearing protection arrangement which achieves increased sound attenuation through the use of component elements of differing mechanical resonance frequencies.

Additional objects and features of the invention will be understood from the following description and the accompanying drawings.

These and other objects of the invention can be achieved by sound attenuating ear protection apparatus which includes an air evacuated sealed chamber member disposable between the eardrum of the user subject and an ear external source of intense sound and means for establishing a sound-tight seal between the evacuated chamber member and the skin tissue of the user subject.

BRIEF DESCRIPTION OF THE DRAWINGS

FIG. 1 is a cross-sectional view of a hearing protection headset having protective cup seal members capable of surrounding the external ears of a user.

FIG. 2 is an alternate arrangement of the hearing protection invention embodied in the form of an element disposable in the outer portion of a user's external ear.

FIG. 3 is an alternate arrangement of the hearing protection invention arranged for disposition within the ear canal of the user.

DETAILED DESCRIPTION

FIG. 1 of the drawings shows a pair of externally wearable hearing protection devices made in accordance with the present invention. The FIG. 1 hearing protection devices 100 and 102 each include a pair of cup-like shell members—104 and 112 of generally spherical shape for the right hand protector 100, and 106 and 114 for the left hand protector 102. The cup-like shell members 104 and 112 meet in a junction or interface 116. The junction or interface for the protector 102 is indicated at 118 in FIG. 1. The junctions or interfaces 116 and 118 may, as shown in FIG. 1, be located in and disposed perpendicular of the flanges 134 and 136.

The cup-like inner shell members 104 and 106 each define enclosed region 108 and 110 which accommodate the exterior ear structures of the hearing protection user. The enclosed regions 108 and 110 can, of course, be adjusted in size and shape to optimize the FIG. 1 apparatus for particular uses and users and can even be individualized for different users if needed.

The resilient pad members 120 and 122 in FIG. 1 can be of substantially annular shape, and serve to seal the interface between the annular flanges 134 and 136 of the protective devices 100 and 102 and the skin tissue of a user. The resilient pad members 120 and 122 may be fabricated of foam rubber, flexible plastic, inflated structures or other soft and pliable materials, as is known in the ear protection and headphone art.

As shown in FIG. 1, the inner and outer cup-like shell members 104 and 112, 106 and 114 are of different size and configuration—an arrangement which defines a pair of closed cavity interior spaces 124 and 126 intermediate the shell member adjacent walls. According to the present invention, the closed cavity interior spaces 124 and 126 are evacuated of air in order to block or attenuate sound energy originating external of the protective devices 100 and 102. Use of an evacuated space or a vacuum plenum as a sound energy attenuating medium is in accordance with the principle of physics which indicates that sound is not transmitted through a vacuum since in a vacuum there is an absence of compression wave transmitting media.

The presence of a vacuum in the closed cavity interior spaces 124 and 126 requires that the shell members 104, 106, 112, and 114 be fabricated of such materials and shaped in such configurations as provide capability for withstanding the considerable force of atmospheric pressure spread over the shell member surfaces.

A variety of materials may be used in fabricating the protection devices 100 and 102 in FIG. 1, to achieve this needed structural integrity. Such materials include generally substances in the families of metals, glasses, ceramics, and plastics. Metals such as stainless steel and brass are particularly attractive from a fabrication viewpoint for constructing the FIG. 1 hearing protection devices, since the usual fastening techniques of welding, brass brazing, and brass soldering are thereby made available. Evacuated structures of the general complexity of the FIG. 1 protection devices are commonly fabricated in stainless steel, as is exemplified by the all stainless steel vacuum bottle currently sold in the sporting goods and household markets. Brass structures of the general complexity of the FIG. 1 protection devices have commonly been employed as the temperature and pressure responsive element in thermostats, barometers, altimeters and similar instruments, and were until recently used in automobile engine temperature control thermostats. Brass materials have the advantage of being more readily soldered or brazed than are stainless steel materials—tungsten inert gas (TIG) welding is, however, a feasible attachment arrangement when stainless steel shell members are used in FIG. 1.

When fabrication of glass or glass-like materials is employed in the FIG. 1 protectors, heated fusion sealing as has been practiced in the glass blowing art may be used in integrating the inner and outer cup-like shell members into a unitary structure at the interfaces 116 and 118. The glass-like materials used in unbreakable tableware are potential candidates for such fabrication of the protection device shell members in FIG. 1. The Corelle ® glassware sold by Corning Glass Incorporated is an example of such glass-like materials. Corelle ® is a registered trademark of Corning Glass Incorporated.

The use of plastic materials in fabricating the shell members 104, 106, 112, and 114 requires selection of plastics which are of sufficient density as to be impervious or resistant to impact and resistant to diffusion leakage into the evacuated closed cavity interior spaces 124 and 126, such materials as high-density propylene and nylon are considered feasible for this purpose. Since even the best of such plastic materials available are subject to slow diffusion leakage, periodic recharging or maintenance of plastic embodied versions of the FIG. 1 apparatus may be necessary to maintain optimum user hearing protection.

Alternate physical arrangements of the protection devices 100 and 102 in FIG. 1 are, of course, possible for manufacturing convenience or other purposes. In one such alternate arrangement, the shell member flange portions 134 and 136 which are shown to be fabricated as two half-flange annular extending rings 135 and 137 attached to the inner shell member 106 and the outer shell member 114 respectively, could be fabricated as a unitary annular ring attached to one of the shells 106 or 114. In such an arrangement, the weld or braze connection between the annular ring and the shell member occur at a cross-sectional corner, i.e., near the internal or external periphery of one of the shells 106 and 114, and is therefore conveniently accessible. The fabrication and integration of such shell and flange shapes is known in the metal and other material forming arts.

Other variations in the arrangement of the protection devices 100 and 102 to achieve low-cost, reliable fabrication will be apparent to persons skilled in the manufacturing art, for example, the shells 104 and 112 could be fabricated as a single unit through the provision of a large access port in one of the shells and the use of hydraulic forming techniques or molding and casting techniques. A molded or cast arrangement of the FIG. 1 protection devices might, for example, employ metals such as magnesium, aluminum, or a die-cast alloy of zinc and aluminum composition. Molding and casting fabrication of the FIG. 1 protection devices could also be used with the previously described glass, ceramic, and plastic materials. An access port for removing mold materials as, for example, by flushing, would be required to provide empty space in the closed cavities 124 and 126 in such a fabrication arrangement.

The FIG. 1 hearing protection apparatus may also be fabricated as a composite structure using different materials. In such an arrangement the outer shells 112 and 114 may be fabricated of metal and the inner shells 104 and 106 made from a glass or ceramic material, for example. Such an arrangement leads well to the separated resonant frequencies concept discussed below. The sealing of glass and metal elements into an air-tight integral structure can be achieved in the manner employed in the vacuum tube and hermetically sealed refrigeration compressor arts.

Following fabrication of the hearing protection devices 100 and 102 from any of the possible materials and using any of the possible fabrication techniques, evacuation of the closed cavities 124 and 126 is required. A pair of stems 138 and 140 are shown as representative arrangements for achieving such evacuation. The stems 138 and 140 may be connected with a vacuum pump until the suitable degree of high vacuum in the spaces 124 and 126 is achieved, and then the stems pinched off and sealed as indicated at 142 and 144 to retain the vacuum condition in the cavities 124 and 126. Such evacuation and pinch-off are similar to techniques used in the vacuum tube, light bulb, and refrigeration system arts. The stems 138 and 140 may be recessed or located in positions of greater user convenience than are the drawing convenience positions of FIG. 1.

In the FIG. 1 hearing protection apparatus, it is desirable for the mechanical resonance frequency of the inner shell members 104 and 106 to differ from the mechanical resonance frequency of the outer shell members 112 and 114 in order to minimize the conduction of sound energy between the shell members and thereby maximize the attenuation of noise energy reaching the enclosed regions 108 and 110. In accordance with the relative physical sizes of the inner shell members 104 and 106 and the outer shell members 112 and 114, it is preferable for the inner shell members 104 and 106 to have a higher resonance frequency than that of the larger outer shell members 112 and 114 in achieving these different resonant frequencies.

The resonance frequency of a shell member is influenced by the type of material used in fabricating the shell member, the thickness of this material, and the physical configuration of the shell member. A shell member may, of course, have multiple mechanical resonance frequencies and in such instance the separation of inner shell resonance frequencies from those of the outer shell members is yet desirable. A mechanical resonance frequency for a given shell material and configuration can be lowered if necessary, to provide the desired separation between inner and outer shell members by the addition of mass to the shell member. Such mass addition can be accomplished by the attachment of supplemental masses within the closed cavities 124 and 126 as needed. The resonance frequency of a shell member is also influenced by the effective spring constant of the shell member structure, such spring constants can, of course, be altered through the use of material selection or mechanical working variations of the selected material.

The presence of the evacuated closed cavities 124 and 126 adds materially to the thermal insulating properties of the FIG. 1 protective devices. The thermal insulating properties are of special interest when hearing protection devices are used in cold climates or at high altitudes or when artificial cooling or heating is to be employed in the enclosed regions 108 and 110. The glass, ceramic, and plastic materials described earlier for fabrication of the shell members comprising the protection devices 100 and 102 are, of course, preferable for use where thermal insulation properties of the hearing protection devices is important.

For applications wherein communication with the user of the FIG. 1 hearing protection apparatus is needed, an electrical-to-acoustic transducer device such as a magnetically excited movable diaphragm or a piezoelectric crystal device may be mounted within the enclosed regions 108 and 110 in order that the FIG. 1 apparatus also function in the manner of a pair of headphones. Alternately, a stethoscope-like acoustic coupling tube can be disposed in communication with the enclosed regions 108 and 110, and connected with external transducer devices. The stethoscope-like tube or electrical conductors for a transducer element may be disposed around the flanges of the protection devices 100 and 102, that is, through the resilient pad members 120 and 122, or alternately, may pass through the closed cavity interior spaces 124 and 126 with the use of appropriate sealing.

The protection devices 100 and 102 in FIG. 1 are shown to be movably attached to a flexible or resilient headband member 128 by a pair of frictional engagement devices 130 and 132. The frictional engagement devices 130 and 132 are attached to the outer shells 112 and 114 in any convenient manner such as by welding or adhesive attachment. The protection devices 100 and 102 may also be incorporated in a helmet structure or supported by a behind-the-neck flexible tension member in addition to the headband member 128.

An alternate embodiment of the present invention hearing protection apparatus is shown in FIG. 2 of the drawings. The FIG. 2 hearing protection device 206 is shown configured in a form which can be retained in the external ear 200 of a user. To explain this arrangement of the invention, the FIG. 2 drawing includes a simplified cross-section of a segment of a human skull in the region around the ear. In FIG. 2, the skull bony structure is shown at 202, and the user's ear adjacent skin tissue at 203, while the ear canal of the user is indicated at 204, and the eardrum at 205.

The hearing protection device 206 in FIG. 2 is also shown in cross-sectional form and includes an exterior surface portion 214 corresponding to the shells 112 and 114 in FIG. 1, and an interior surface portion 216 corresponding to the shells 104 and 106 in FIG. 1. The cavity 212 in FIG. 2 corresponds to the closed cavity interior spaces 124 and 126 in FIG. 1, while the inner and outer faces of the exterior surface portion 214 are indicated at 208 and 210 in FIG. 2.

The exterior shape of the FIG. 2 hearing protection device 206 is intended to be closely configured to the shape of the user's external ear 200 in order that a good sound-tight seal be attained between the protection device 206 and the ear 200. This seal can also be facilitated with the use of jellies, waxes, or other pliable media intermediate the hearing protection device 206 and the ear 200. The actual shape of the protection device 206 can be closely configured to resemble the shape of the user's ear 200 through the use of impression molding techniques as are commonly used in the dental, hearing aid, and similar arts. An impression molded hearing protection device can be fabricated from the metals, glasses, ceramics, and plastics described for the FIG. 1 apparatus, and can be cast or molded as is commonly achieved in the impression molding art.

The cavity 212 of the FIG. 2 protection device can be evacuated through the use of a stem member of the type shown at 138 and 140 in FIG. 1, or through some alternate interior communicating arrangement, neither of which are shown in FIG. 2, but are known in the art.

The inherent dissimilarity of sizes of the exterior surface 214 and interior surface 216 in FIG. 2 lend well to the achievement of different mechanical resonant frequencies for the surfaces 214 and 216, as was indicated to be desirable for the shell members 104 and 112, 106 and 114 in FIG. 1. The larger physical size of the exterior surface 214 makes the attainment of lower resonance frequency for this surface in comparison with the surface 216 convenient.

Although the space between the inner and outer faces 208 and 210 of the exterior surface 214 i.e., the thickness of the exterior surface 214 or its cross-section is shown in FIG. 2 to be appreciable, such showing is principally for drawing convenience. A practical embodiment of the FIG. 2 hearing protection device is preferably arranged to have a thin cross-section in the interests of mass reduction, minimal sound conduction and reduced heat transmission. It is, of course, desirable for the protection device 206 to be of assured mechanical integrity in order that the user's eardrum 205 and other ear elements be protected from accidental rupture of the evacuated cavity 212 which is inherently located in close proximity to sensitive and fragile ear elements.

In most instances of using the protection device of FIG. 2, complementing hearing protectors in the left and right ear of the user are preferred. Preferably each of these protection devices is individually fabricated from an impression of the intended use ear in order that the most effective sealing between the protection device and the user's ear tissue result; desirably such sealing is achieved without the aid of the previously mentioned jellies or other assistance media.

Protection devices of the type shown at 206 in FIG. 2 can be held in place either by a close mechanical interface with the user's ear portions or alternately, can be assisted in being held in position through the use of ear- or head-mounted supporting devices of the general nature of the headband 128 in FIG. 1. If used, the jelly, wax or other sealing medium described above can also assist in retaining a FIG. 2 type protection device in position.

The FIG. 2 hearing protection device is intended primarily for residence in the user's external ear with minimal projection into the ear canal. In contrast with this arrangement, the hearing protection device 306 in FIG. 3 is intended principally for residence within the user's ear canal 304. Each of the elements 300-316 in FIG. 3 corresponds to the similarly numbered elements in FIG. 2, except for discernible differences in sizes and shapes. These FIG. 2 similar elements in FIG. 3 include the external ear 300, the skull bony structure 302, the previously mentioned ear canal 304 and protection device 306, along with the inner and outer protection device faces 308 and 310, the cavity 312 and the exterior and interior surfaces 314 and 316. An evacuation port or stem as indicated at 138 and 140 in FIG. 1 is, of course, also necessary for the FIG. 3 hearing protection device, and may be provided in the exterior surface 314 or in other convenient locations of the FIG. 3 protection device.

Sealing of the FIG. 3 protection device 306 with the user's ear canal can, of course, be aided with the use of jellies or other resilient media, but is preferably achieved through reliance on a close mechanical conformance of the protection member 306 with ear canal surface. A protrusion or other grippable device from the exterior surface 314 end of the protection device 306 may be used as an assistance in inserting and removing the protection device from the ear canal. The mechanical resonance frequency differences and cross-sectional considerations indicated above for FIG. 2 are also pertinent to the FIG. 3 protector.

The extended length of the FIG. 3 hearing protector is desirable for decreasing the vibrational coupling between exterior and interior surfaces 314 and 316 in the FIG. 3 arrangement of the invention. The relatively long sidewall surfaces of the FIG. 3 protector are helpful in reducing any sound energy reflections within the cavity 312 and in dissipating cross-section conducted sound energy into the non-sound responsive ear canal tissue of the user.

As was the case in the FIGS. 1 and 2 embodiments of the invention, the use of an evacuated cavity intermediate the user's eardrum 305 and the noise environment existing at the exterior surface 314 achieves significantly better attenuation of acoustic energy than has heretofore been possible in a hearing protection apparatus. High frequency sounds as are encountered in the testing and operation of jet aircraft engines are especially amenable to attenuation with hearing protection devices of the type described herein.

Although three arrangements of the hearing protection device have been described herein, other arrangements of the invention are possible. Such other arrangements might include, for example, a stacked array of evacuated chamber wafer members wherein each wafer has the overall appearance of, for example, a silver dollar. With such an arrangement the increased attenuation advantages of a sequential plurality of attenuating chambers is achieved. Alternately, a plurality of adjacently located individually evacuated chambers could be disposed in the shape of a FIG. 1, 2 or 3 apparatus. Other arrangements of the invention may appear to persons skilled in the art.

While the apparatus and method herein described constitute a preferred embodiment of the invention, it is to be understood that the invention is not limited to this precise form of apparatus or method, and that changes may be made therein without departing from the scope of the invention, which is defined in the appended claims.

I claim:

1. Sound attenuating ear protection apparatus comprising:
   a pair of air evacuated, sealed chamber members disposably covering the ears of a user to lie between the user eardrums and an ear external source of undesirable sound energy;
   said air evacuated sealed chamber members each including first and second smooth surface portions with each surface portion having a spherical segment terminated by an annular flange lip shape and being disposable over one external ear of said user with one spherical segment, adjacent said ear being of different, higher mechanical resonance frequency with respect to the other spherical segment distal of said ear;
   said surface segment distal of said ear also including air evacuation stem members and a pinchoff seal therefor;
   said annular flange lips of said first and second surface portions being joined together in a junction disposed intermediate of said first and second spherical surface portions and perpendicular of said flange lips;

resilient suspension means engaged with the head of said user and with said sealed chamber members for supporting said sealed chamber members in selected position over said user external ears; and resilient sealing means disposable intermediate said evacuated sealed chamber member flange portion and the cranial surface skin tissue of said user for establishing a sound-tight seal between said evacuated chamber member and the skin tissue of said user.

2. The apparatus of claim 1 wherein said evacuated sealed chamber member includes an exterior surface portion receivable within the ear of said user subject.

3. The apparatus of claim 2 wherein said ear receivable exterior surface portion is configured for reception within the ear canal of said user subject.

4. The apparatus of claim 2 wherein said air evacuated sealed chamber comprises an ear plug member receivable within the ear canal of said user subject and wherein said means for establishing an air-tight seal includes ear canal shaped subportions of said exterior surface portion.

5. Hearing protection apparatus disposable about the head of a test subject and covering the external ears thereof, for diminishing the intensity of noise sounds received in said ears, comprising:

a pair of first continuous spherically curved cup-shaped interior shell members having an integral outward directed annular flange curvature termination portion located at the cup rim region thereof and disposition, one covering each said external ear of said test subject;

a pair of second continuous spherically curved cup-shaped exterior shell members having an integral inward directed annular flange curvature termination portion located at the cup rim region thereof and disposed one each over each of said first continuously curved cup-shaped interior shell members in annular flange junction contact therewith to define a pair of closed cavities intermediate said shell members, said closed cavities intervening the path of said noise sound to each of said ears;

said interior shell and exterior shell members having higher and lower different mechanical resonance frequencies, respectively;

said closed cavities each being air evacuated and thereby of reduced sound transmission capability; and sealing means engageable with one of said shell members at the annular flange extent thereof, and with the head of said test subject for inhibiting noise sound transmission around said air evacuated cavities to said test subject ears.

* * * * *